US009636188B2

United States Patent
Gattani et al.

(10) Patent No.: US 9,636,188 B2
(45) Date of Patent: May 2, 2017

(54) SYSTEM AND METHOD FOR 3-D TRACKING OF SURGICAL INSTRUMENT IN RELATION TO PATIENT BODY

(75) Inventors: Abhishek Gattani, San Jose, CA (US); Salmaan Hameed, San Jose, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 2795 days.

(21) Appl. No.: 11/388,756

(22) Filed: Mar. 24, 2006

(65) Prior Publication Data
US 2007/0225550 A1    Sep. 27, 2007

(51) Int. Cl.
A61B 34/20        (2016.01)
*A61B 90/00*        (2016.01)
*A61B 90/10*        (2016.01)
*A61B 34/10*        (2016.01)

(52) U.S. Cl.
CPC .............. *A61B 90/36* (2016.02); *A61B 34/20* (2016.02); *A61B 34/10* (2016.02); *A61B 90/10* (2016.02); *A61B 90/361* (2016.02); *A61B 2034/102* (2016.02); *A61B 2034/2051* (2016.02); *A61B 2090/363* (2016.02); *A61B 2090/364* (2016.02); *A61B 2090/371* (2016.02); *A61B 2090/376* (2016.02); *A61B 2090/3983* (2016.02)

(58) Field of Classification Search
CPC ...... A61B 2034/102; A61B 2034/2051; A61B 2090/363; A61B 2090/364; A61B 2090/371; A61B 2090/376; A61B 2090/3983; A61B 34/10; A61B 34/20; A61B 90/10; A61B 90/36; A61B 90/361
USPC .......................... 600/407, 409, 424; 601/1–3
See application file for complete search history.

(56) References Cited

U.S. PATENT DOCUMENTS

| 6,016,439 | A  | * | 1/2000 | Acker ............................ 600/411 |
| 6,233,476 | B1 | * | 5/2001 | Strommer et al. ............ 600/424 |
| 6,754,596 | B2 |   | 6/2004 | Ashe |
| 2002/0049375 | A1 |   | 4/2002 | Strommer et al. |
| 2002/0082498 | A1 | * | 6/2002 | Wendt et al. ................. 600/411 |
| 2004/0215071 | A1 | * | 10/2004 | Frank et al. .................. 600/407 |

(Continued)

FOREIGN PATENT DOCUMENTS

| EP | 1 415 609 A1 | 5/2004 |
| EP | 1 519 140 A1 | 3/2005 |

(Continued)

OTHER PUBLICATIONS

International Search Report dated Jan. 2, 2008.

*Primary Examiner* — Patricia Park
*Assistant Examiner* — Vani Gupta
(74) *Attorney, Agent, or Firm* — Flynn, Thiel, Boutell & Tanis, P.C.

(57) ABSTRACT

A system and method for tracking the three-dimensional position and orientation of a surgical instrument as the instrument is being utilized within the interior of a patient body. A stereoscopic camera system generates a stereoscopic image of the patient body which is subsequently rendered on a display device. A wireless signal transmitted by an electromagnetic field generator is received by a sensor on the surgical instrument. Utilizing this sensor data, a processor calculates the position and orientation of the surgical instrument and then superimposes upon the rendered stereoscopic image of the patient body a graphical representation indicative of the position and orientation of the surgical instrument.

29 Claims, 12 Drawing Sheets

(56) References Cited

U.S. PATENT DOCUMENTS

| | | | |
|---|---|---|---|
| 2004/0254454 A1* | 12/2004 | Kockro | 600/424 |
| 2005/0165276 A1* | 7/2005 | Belson et al. | 600/146 |
| 2006/0258938 A1* | 11/2006 | Hoffman et al. | 600/424 |

FOREIGN PATENT DOCUMENTS

| | | |
|---|---|---|
| WO | WO 00/69335 | 11/2000 |
| WO | WO 2004/001569 A2 | 12/2003 |
| WO | WO 2005/087125 A2 | 9/2005 |

\* cited by examiner

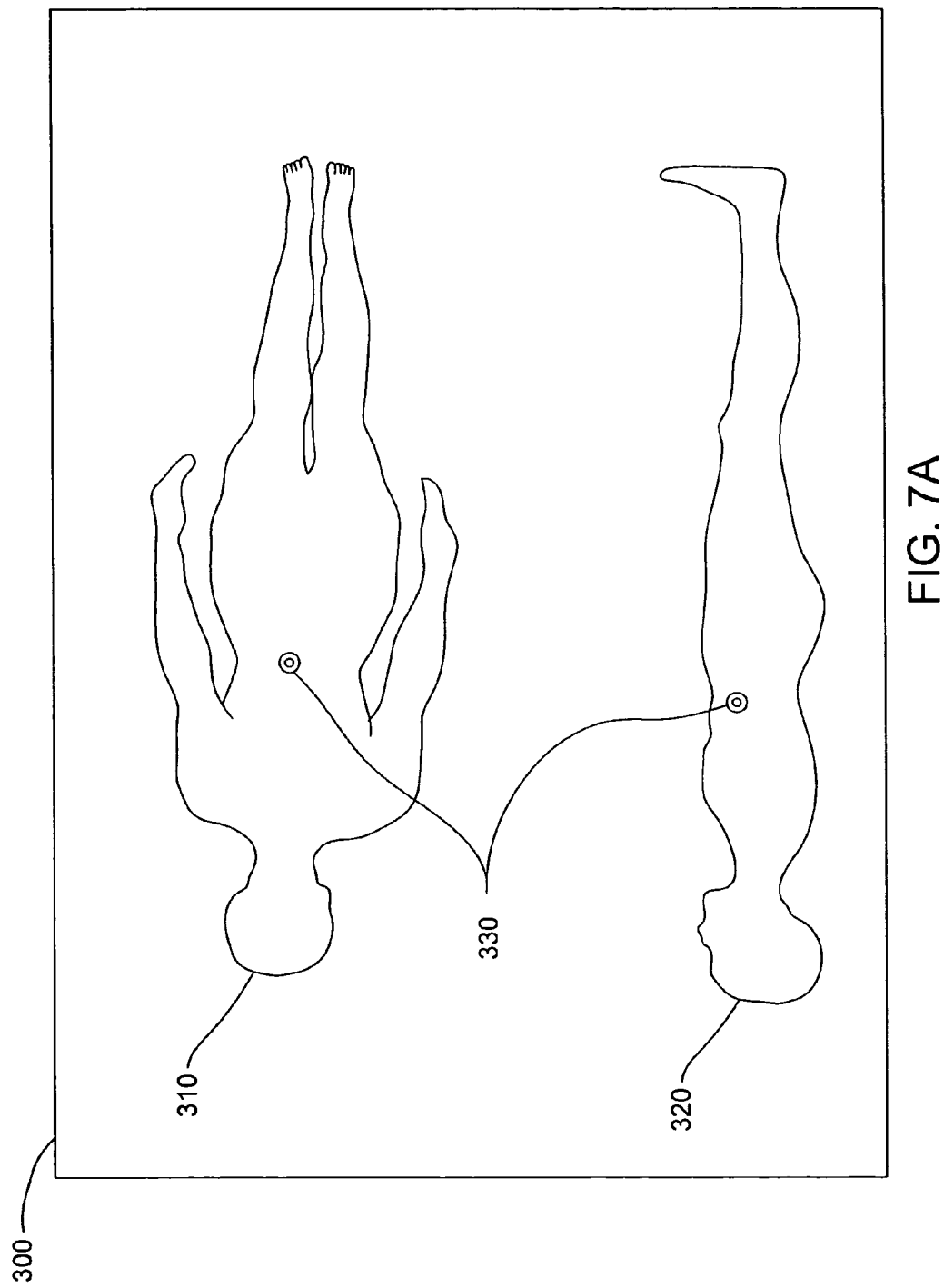

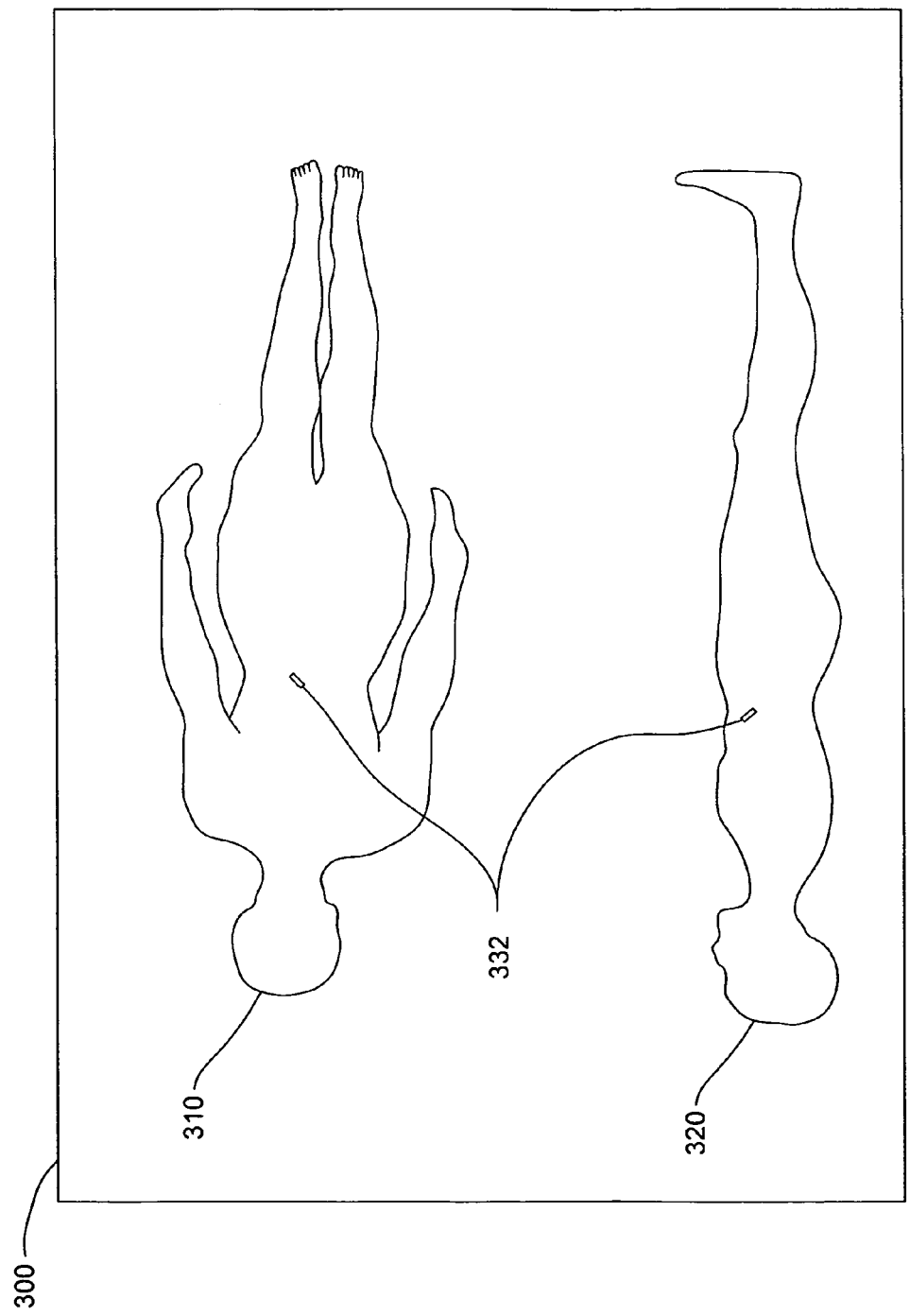

SYSTEM AND METHOD FOR 3-D TRACKING OF SURGICAL INSTRUMENT IN RELATION TO PATIENT BODY

FIELD OF THE INVENTION

The present invention relates to a system and method for wirelessly tracking an instrument and, more specifically, to a system and method for wirelessly tracking a three-dimensional position and orientation of a surgical instrument in relationship to the body of a patient being operated upon.

BACKGROUND OF THE INVENTION

A primary goal of minimally invasive surgical procedures is to minimize the adverse effects of the procedure on the patient. This reduces post-surgical trauma and pain and minimizes recovery time. Some minimally invasive procedures require the surgeon to create one or more small incisions through which various surgical instruments can be passed. Other minimally invasive procedures forego the need to make even small incisions in the patient, instead relying on surgical instruments such as, for example, flexible endoscopes that can enter the body through a natural bodily orifice.

FIGS. 1 and 2 depict a traditional flexible endoscope 20 which can be utilized by a surgeon to remotely view and manipulate tissue within the body of a patient. As illustrated in FIG. 1, a traditional flexible endoscope 20 generally comprises a control body 22 that connects to an insertion tube 24. The control body 22 remains outside the patient, while the flexible insertion tube 24 is inserted into the interior of the patient via either a naturally occurring or man-made orifice. Depending on the intended function of a specific flexible endoscope, the insertion tube 24 can include, for example, various channels for performing suction, biopsy, irrigation and insufflation. The insertion tube 24 may also include fiber optics or light bundles for conveying light from an external light source to the interior of the patient, as well as conveying images from the interior to an exterior camera. A connector 32 allows the endoscope 20 to connect to one or more various related system components, including, for example, a power supply, a light source, a camera and/or video processor. Endoscope 20 may also include additional control means 30 for controlling one or more functions of the endoscope, such as, for example, a manipulator or other tissue processing means that extends out from the distal tip section 26 of the endoscope 20.

In practice, the insertion tube 24 is inserted into an orifice of the patient and then slowly advanced into the interior of the patient. One or more controls 28 typically located on the body 22 of the endoscope 20 allows for the surgeon to manipulate or bend the distal tip section 26 of the flexible endoscope as he or she advances the insertion tube 24 through the patient. In this manner, the surgeon can steer the tip 26 of the endoscope as it is advanced through the interior of the patient's body.

Thus, as illustrated in the example of FIG. 2, a surgeon can utilize a flexible endoscope 20 to view and manipulate the tissue of a patient's upper gastrointestinal tract by inserting the distal tip section 26 of the endoscope 20 into the mouth 44 of the patient 42. The surgeon then advances the insertion tube 24 down the patient's esophagus 46 until the tip region 26 of the endoscope 20 is in the region of tissue that he or she wishes to examine, i.e., the stomach 48 or duodenum 50.

However, a problem that exists in most applications involving a flexible endoscope is that the area of tissue or target anatomy that the surgeon wishes to examine and manipulate is often an area that is not in the immediate proximity of the natural orifice used to gain access to the interior of the patient's body. As such, the surgeon is often required to navigate the surgical instrument, such as the flexible endoscope, to the target anatomy and operate on portions of the anatomy that are neither directly visible nor readily visible without some degree of difficulty. Furthermore, even though surgical instruments such as flexible endoscopes do allow for a surgeon to remotely view and manipulate tissue, they are limited in their capabilities and difficult to master. For instance, endoscopes typically have limited field of view. In addition, they display anatomical data in two dimensions. As a result, even an experienced surgeon can find it difficult to navigate to a specified area of tissue and localize a specific target region, such as an organ or lesion. Moreover, the level of difficulty involved in navigating to a target tissue increases significantly as the distance between the target tissue and the orifice used to gain entry to the interior of the patient increases.

SUMMARY OF THE INVENTION

A system and method for tracking the three-dimensional position and orientation of a surgical instrument, as the instrument is being utilized within the interior of a patient body, including a stereoscopic camera system which generates a stereoscopic image of the patient body, which image is subsequently tendered on a display device. A wireless signal transmitted by an electromagnetic field generator is received by a sensor on the surgical instrument. Utilizing this sensor data, a processor calculates the position and orientation of the surgical instrument and then superimposes upon the rendered stereoscopic image of the patient body a graphical representation indicative of the position and orientation of the surgical instrument.

According to another embodiment, the position and orientation of a surgical instrument is wirelessly determined. A projector, such as a low-powered laser, then projects a pattern of light upon the patient body that visually indicates the position and/or orientation of the surgical instrument in real-time as the instrument is being utilized within the interior of the patient body.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which:

FIGS. 7A-7C are illustrative examples of the type of information rendered upon a display by the present invention according to various alternative embodiments.

DETAILED DESCRIPTION

Figure 1:
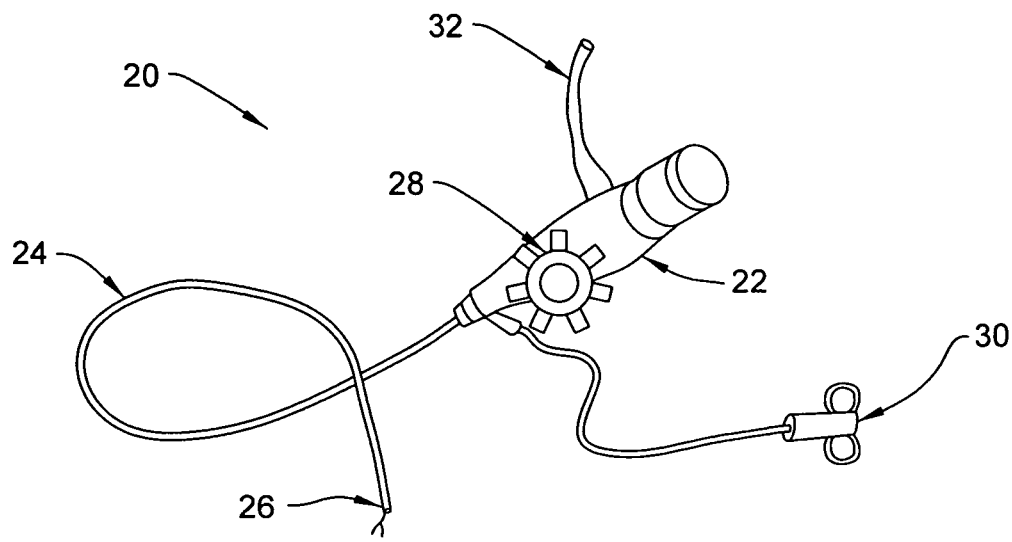
FIG. 1 illustrates a traditional flexible endoscope.
Figure 2:
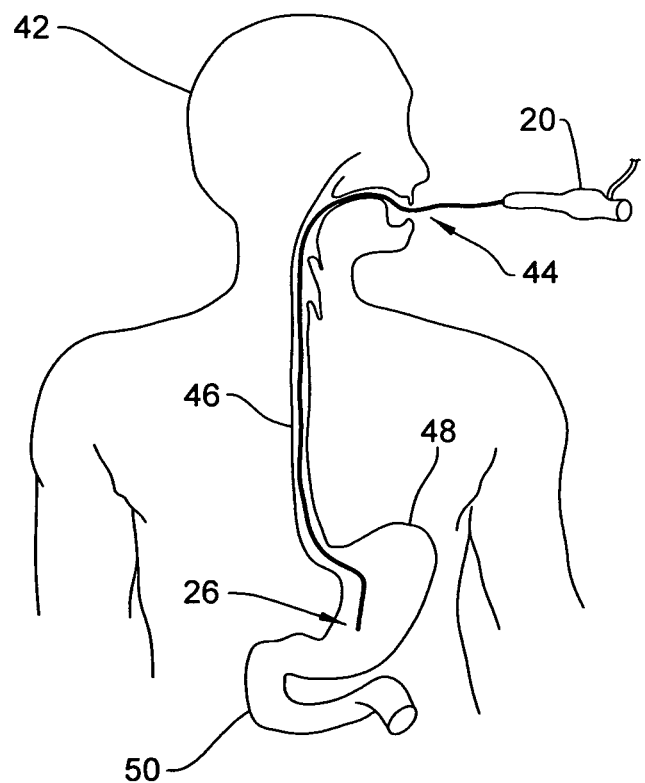
FIG. 2 illustrates the use of a flexible endoscope to examine and/or manipulate the tissue of a patient's upper gastrointestinal tract.
Figure 3:
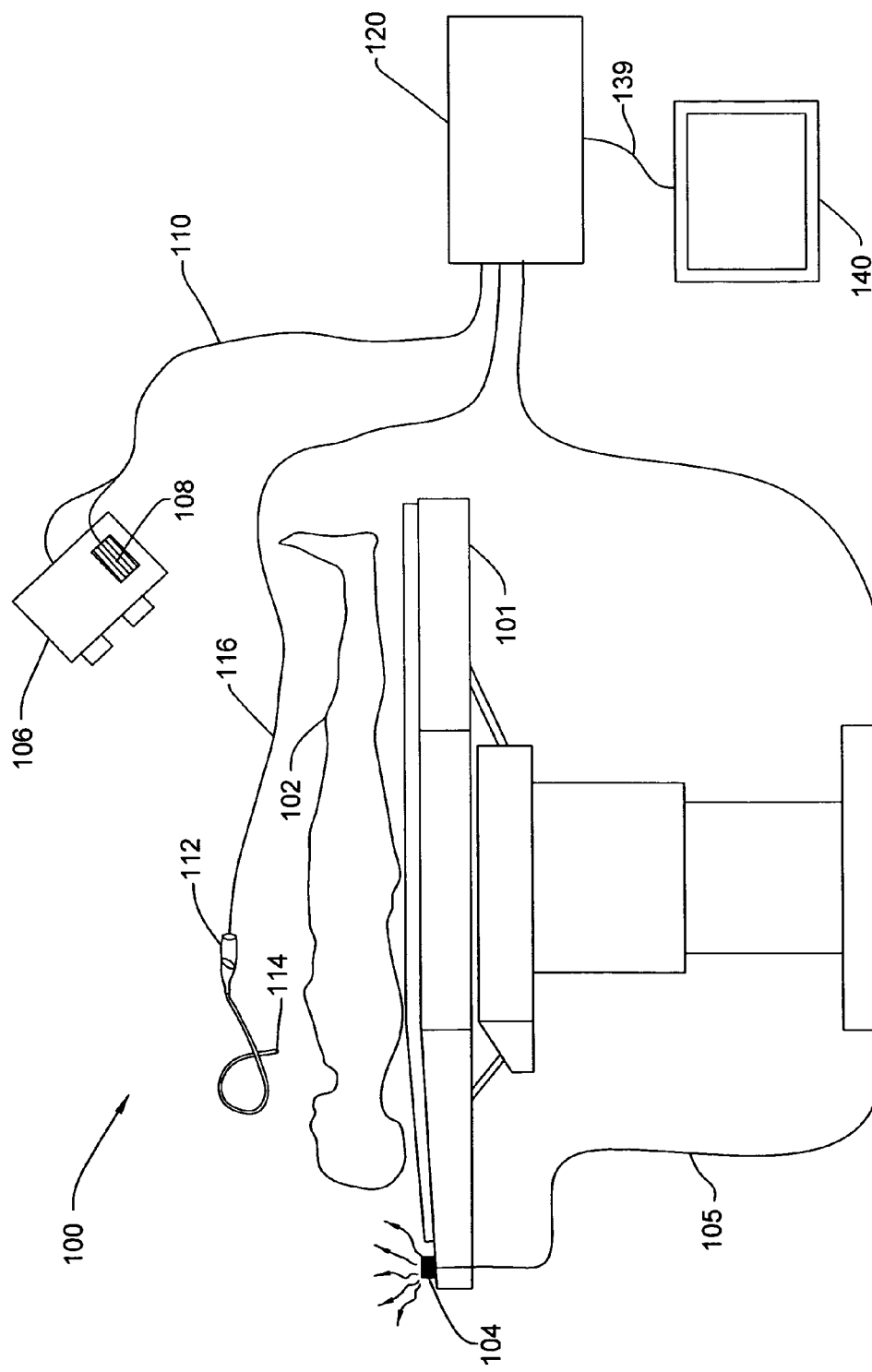
FIG. 3 illustrates a system for tracking the 3-D position and orientation of a surgical instrument according to one embodiment of the present invention.

FIG. 3 depicts a system 100, according to a first embodiment, for tracking the three-dimensional position and orientation of a surgical instrument in relation to the body 102 of a patient lying on a surgical table 101.

An electromagnetic field (EMF) generator 104 communicates with a central controller 120 by means of a hard-wire connection 105. Alternatively, the EMF generator 104 could be configured to communicate wirelessly with the central controller 120 by means of one or more proprietary or standardized wireless communication protocols, such as, for example, various infrared communication protocols, Bluetooth wireless protocol, and 802.11 a/b/g protocols, to name a few. The EMF generator 104 can be positioned at various locations within the operating room around the patient. For example, the EMF generator 104 can be incorporated with or mounted upon the surgical table 101 so as to be located at the head, middle or foot section of the surgical table 101. Alternatively, the EMF generator could be incorporated with or mounted upon other components near the surgical table 101 within the operating room, such as, for example, an overhead boom or independent stand. However, regardless of location, the EMF generator 104 should be maintained in a fixed position relative to the patient once the system 100 is in use.

Also included in the system 100 is a stereoscopic camera system 106 for generating a stereoscopic image of the body of the patient. The stereoscopic camera 106 operates on the principle of stereopsis, wherein two images of a scene are generated from different perspectives, the two images representing independent left eye and right eye views of the scene. The two images are then displayed such that the left eye sees only the left eye view and the right eye sees only the right eye view. The slightly different perspectives of the images that the human eyes see are re-created, resulting in an overall image of the scene which appears three-dimensional.

More specifically, a stereoscopic image is generated according to a process known as perspective projection. The perspective projection process involves calculating what a three-dimensional scene would look like from the point of view of an arbitrary location, such as, for example, the location of a camera, in 3-D space. Perspective refers to the fact that more distant objects end up looking smaller, and the fact that parallel lines in the three-dimensional world may not end up looking parallel in a two-dimensional perspective projection.

Figure 4:
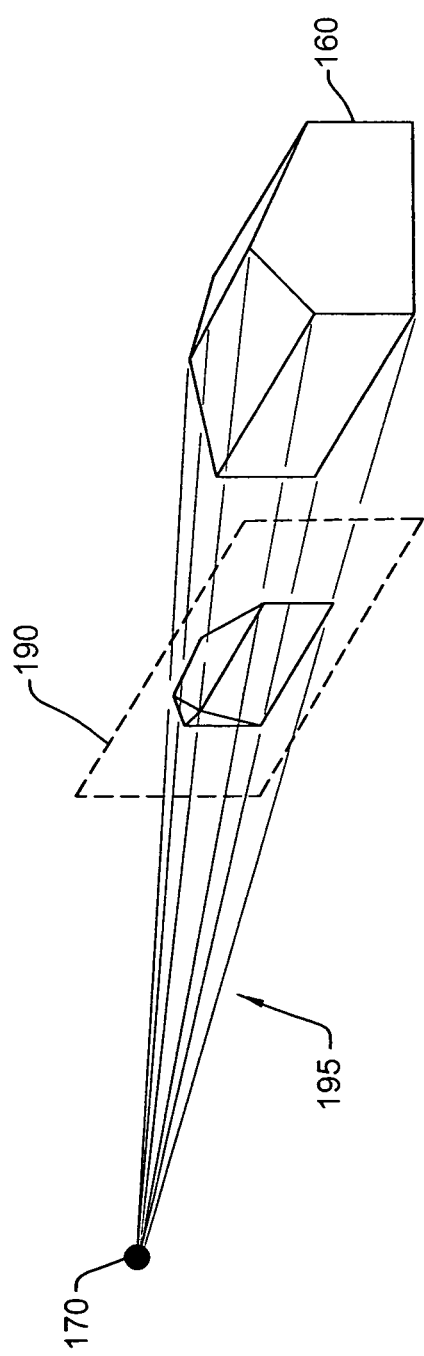
FIG. 4 is an illustrative example of perspective projection.

An illustrative example of perspective projection is provided by FIG. 4, which depicts how an object 160 is viewed from a single point 170 in three-dimensional space. The visual rays of light reflecting off of, or projecting from, the object 160 converge at the point 170. The representation of the transparent plane 190 can be considered the view that would be seen by a single eye (i.e., the left eye) at a known point in space. The image is formed on the transparent plane 190 by the intersecting points of the projecting lines 195 from the point 170 (i.e., the eye) to the object 160. Acquiring a second view from a different point in space (i.e., the right eye) would result in a second transparent plane and associated image (not illustrated). The human mind subsequently interprets corresponding first and second images from different perspectives as a three-dimensional view of a scene.

In the current example, camera 106 incorporates or has attached thereto an EMF sensor 108 that is capable of detecting the wireless electromagnetic signal being transmitted by the EMF generator 104. Camera 106 and associated sensor 104 communicate with the central controller 120 via an associated wire connection 110. Alternatively, camera 106 and associated EMF sensor 108 could be configured to communicate wirelessly with the central controller 120, much like the EMF generator 104 as previously discussed.

Also connecting to the central controller 120 via either an associated wire connection 139 or wirelessly is a display means or device 140 capable of depicting to the surgeon the stereoscopic image or images of the patient body 102 taken by the camera system 106. The display means 140 can render multiple two-dimensional images of the patient body 102 which, when taken as a whole, allow for the identification of a three-dimensional point in space with respect to the patient body 102.

Two different methods exist for displaying the two views making up a stereoscopic image, including a time-parallel method and a time-multiplexed method. In one embodiment, the display means 140 operates according to the time-parallel method, displaying both left and right views simultaneously, such as, for example, by a split screen or dual screen system. According to this method, the surgeon wears polarizing or filtering glasses to ensure that the appropriate view is seen by the correct eye. Alternatively, the surgeon can be accommodated with a head mounted display that is configured to project the left and right images to the surgeon's left and right eyes, respectively. According to one example, the head mounted display achieves its projection pattern by incorporating separate left and right displays for the left and right eyes, respectively.

In an alternative embodiment, the display means 140 operates according to the time-multiplexed method, where the same display alternates between depicting a left view of a scene and a corresponding right view of the scene.

Regardless of operating method, the display means 140 can comprise one or more digital displays such as LCD screens or the like. Alternatively, the display means 140 could comprise one or more projectors or any other means for visualizing an image, ranging from simple display technology to more complicated digital display devices such as a "heads-up" display or head mounted display previously discussed.

Also included in the system 100 are one or more surgical instruments 112 for visualizing and/or manipulating the tissue of a patient. Incorporated within or mounted upon at least a distal tip of the surgical instrument 112 is at least one EMF sensor 114 that is capable of detecting the wireless electromagnetic signal being transmitted by the EMF generator 104. The instrument 112 and associated EMF sensor 114 communicate with the central controller 120 via an associated wire connection 116. Alternatively, each instrument 112 and associated EMF sensor 114 could be configured to communicate wirelessly with the central controller 120, much like the EMF generator 104 as previously discussed.

For purposes of example, the remainder of the discussion will reference the surgical instrument 112 as being a flexible endoscope. However, the present invention is not limited to such an application, but could be used in conjunction with various surgical instruments, including but not limited to a catheter, a guide wire, a pointer probe, a stent, a seed, an implant, or an endoscope (including a rigid endoscope, semi-rigid endoscope, or flexible endoscope).

Figure 5:
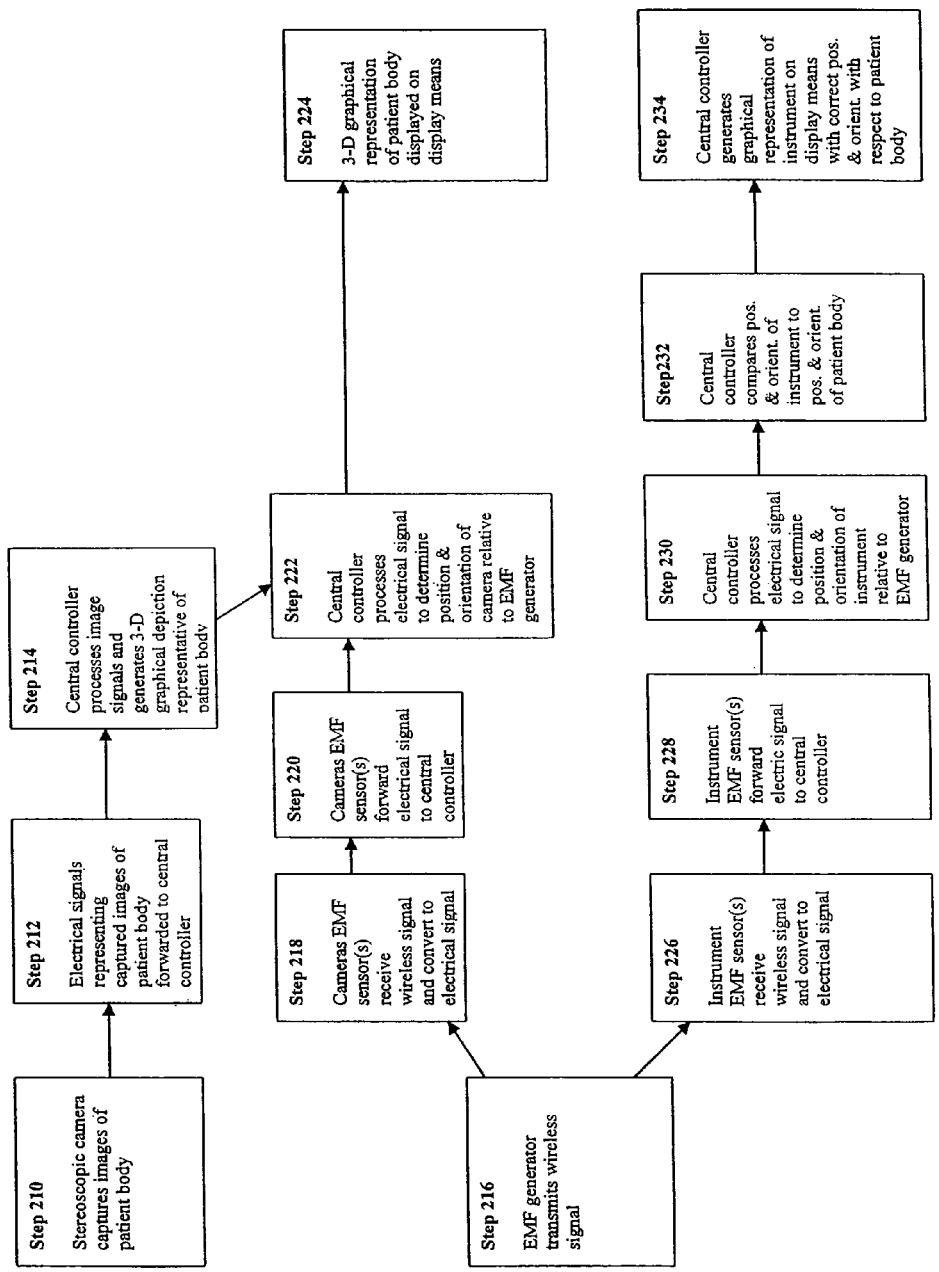
FIG. 5 illustrates a flow chart of the steps involved in tracking the 3-D position and orientation of a surgical instrument according to one embodiment of the present invention.

The basic operation of system 100, as described above, will now be discussed with reference to FIG. 5. After the patient body 102 has been positioned on the surgical table 101, the stereoscopic camera system 106 begins capturing either still or video images of the patient body from two slightly different (i.e., left and right) perspectives (see step 210). Specifically, the camera 106 captures left and right images of the patient body 102 and converts them into electrical signals representing either still or video images (see step 212) and forwards the signals to the central controller 120. The central controller 120 subsequently processes the two signals, representing the left and right images of the patient body 102, respectively, and generates one or more stereoscopic images of the patient body 102 that can be displayed on the display means 140 (see step 214).

Figure 6:
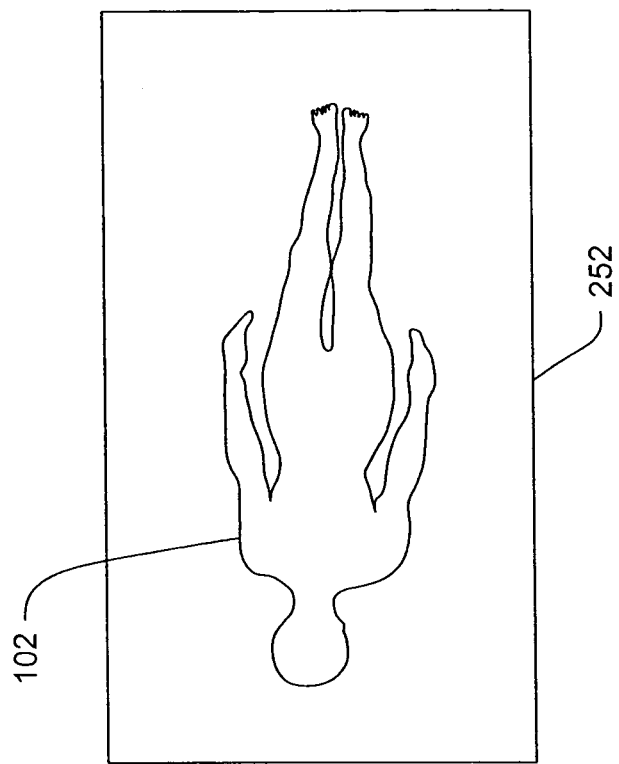
FIG. 6 is an illustrative example of a time-parallel stereoscopic image.
Figure 6:
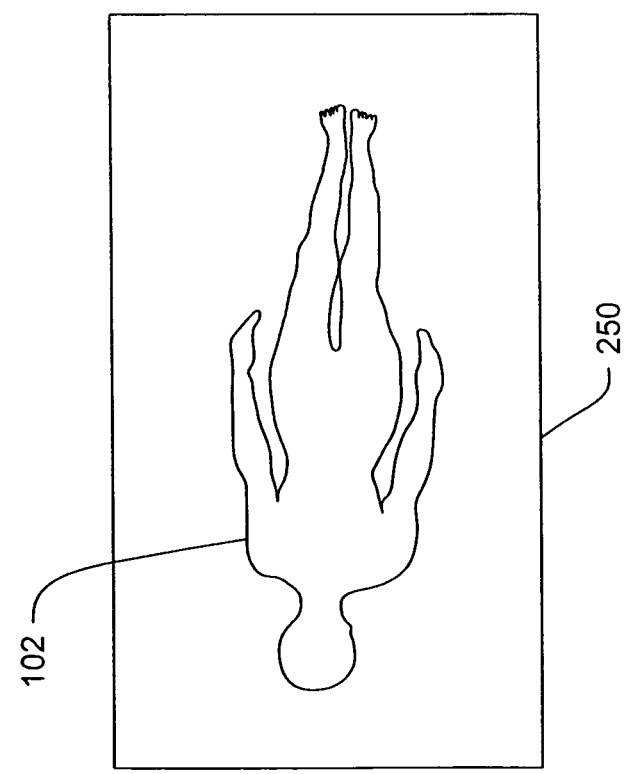

FIG. 6 is an illustrative example of how the stereoscopic image may appear on the display means 140. According to this example, the display means 140 operates according to the time-parallel method, simultaneously displaying both a left image 250 and right image 252 of the patient body 102, the two images 250, 252 representing different views of the patient body 102 taken from slightly different perspectives.

While the right and left views of the patient body 102 are being generated, the EMF generator 104 begins transmitting either a continuous or repeated predetermined wireless signal (see step 216) that travels throughout the area surrounding the surgical table 101. The EMF sensor 108 associated with the camera 106 receives the wireless signal and converts it to an electrical signal that can be subsequently conveyed to the central controller 120 via connection 110 (see steps 218 and 220). The central controller 120 then processes the camera sensor signal upon its receipt using a predefined algorithm that determines the relative position and orientation of the camera EMF sensor 108 with respect to the known position and orientation of the EMF generator 104. This in turn allows for the central controller 120 to determine the relative position and orientation of camera 106 with respect to the EMF generator 104 since the camera EMF sensor 108 is incorporated within or mounted upon the camera 106 in a fixed and known relationship (see step 222). With the above knowledge, the central controller 120 can render on display means 140 a stereoscopic image of the patient body having a known position and orientation with respect to the EMF generator 104 (see step 224).

While the above is occurring, the flexible endoscope 112 begins to be utilized by the surgeon. The EMF sensor 114 located within or upon the tip section of the endoscope 112 also receives the wireless signal being transmitted by the EMF generator 104. Similar to the camera, the endoscope EMF sensor 114 converts the received wireless signal into an electrical signal that is subsequently forwarded on to the central controller 120 via communication link 116 (see steps 226 and 228).

The central controller 120 then processes the electrical signal from endoscope EMF sensor 114 using a predefined algorithm in order to determine the relative position and orientation of the endoscope sensor 114, and thus the relative position and orientation of the tip section of the endoscope 112 itself, relative to the EMF generator 104 (see step 230).

It should be noted that the processing of the sensor signals by the central controller 120 occurs on a near-continuous basis, thereby allowing the central controller 120 to determine the relative position and orientation of both the camera 106 (and thus the patient body 102) and the endoscope EMF sensor 114 at essentially any point in real-time. This is especially important with respect to the endoscope EMF sensor 114, whose position and orientation would presumably be changing frequently as the instrument is utilized by the surgeon. In contrast, the camera 106 and patient body 102 are presumably fixed in position and orientation during the surgical procedure, although this is not a requirement for the current system to function properly.

The central controller 120 subsequently compares the relative position and orientation of the endoscope EMF sensor 114 to the relative position and orientation of the patient body 102 (see step 232). The central controller 120 then superimposes a graphical representation of endoscope 112 (see step 234) upon the stereoscopic image of the patient body rendered on display means 140. Furthermore, this graphical representation of endoscope 112 is updated in near real-time so as to accurately reflect the actual position and orientation of the tip section of endoscope 112 with respect to the patient body 102. The surgeon is thus able to quickly determine the position and orientation of the tip section of the flexible endoscope 112 relative to the patient body by simply glancing at the display means 140 and noting the relative position and orientation of the endoscope tip on the rendered stereoscopic image of the patient body.

Figure 7C:
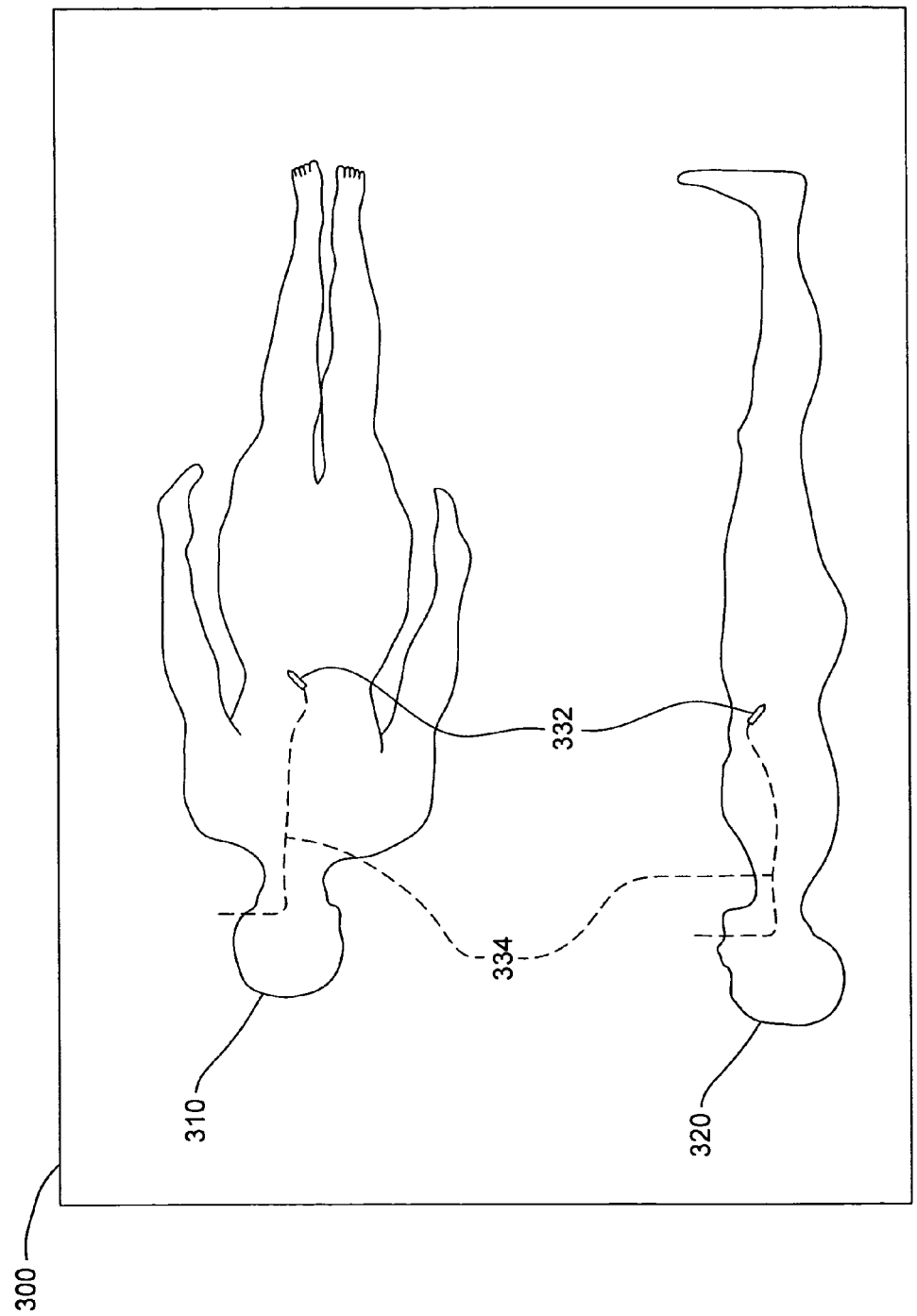

To further clarify how the system described above functions, see FIGS. 7A-7C, which illustrate various examples of a display means 300 depicting a stereoscopic image of a patient body. Note that due to the inherent limitations in depicting three-dimensional images on paper, as well as for purpose of clarity, FIGS. 7A-7C do not depict more conventional stereoscopic images such as that illustrated in FIG. 6. Instead, FIGS. 7A-7C depict relatively unconventional stereoscopic images that comprise two 2-D graphical representations of the patient body taken from significantly different perspectives, with one representation being a top-down view 310 of the body while the other representation is a side view 320 of the body. It should be kept in mind, however, that the embodiments discussed below with respect to FIGS. 7A-7C can be similarly applied to more conventional stereoscopic images such as that depicted in the illustrative example of FIG. 6.

According to the embodiment of FIG. 7A, the location of the endoscope EMF sensor 114 is graphically depicted simply as a dot 330 on the display means 300. As a result, a surgeon can glance at the display means 300 and quickly determine the actual 3-D position (but not orientation in the immediate example) of the endoscope EMF sensor, and thus the 3-D position of the tip section of the endoscope, relative to the patient body even though the surgeon may otherwise not be able to visualize the actual tip of the endoscope.

According to the embodiment of FIG. 7B, the endoscope EMF sensor 114 is graphically rendered on display means 300 as a line, arrow or pointer 332. As a result, the surgeon can quickly glance at the display means 300 and determine the actual 3-D position and orientation of the tip section of the endoscope within the patient body.

According to the alternate embodiment of FIG. 7C, the endoscope EMF sensor 114 is again graphically rendered on the display means 300 as a line, arrow or pointer 332.

However, trailing the pointer 332 is a dotted line 334 which, according to a first sub-embodiment, represents the path that sensor 114 previously traveled before arriving at its current location indicated by pointer 332. In this case, the central controller simply configures the display means 300 to depict prior locations of the endoscope EMF sensor 114 using a different graphical depiction (e.g., dashed or colored line) than that used to indicate a current position of sensor 114 (e.g., arrow or pointer).

According to a second sub-embodiment of FIG. 7C, dotted line 334 represents the actual position of at least a portion of the insertion tube that follows the tip section of the flexible endoscope. To achieve this embodiment, the endoscope incorporates or has mounted thereto a plurality of EMF sensors along at least a portion of the length of the endoscope's insertion tube, with the central controller tracking the position and orientation of each individual EMF sensor.

As shown above, graphical representations of different shapes and sizes can be utilized on the display means to indicate the position and orientation of one or more portions of a surgical instrument such as an endoscope. According to a previous embodiment, a simple graphical representation, such as an arrow or pointer, can be utilized to readily depict the position and orientation of at least a tip section of an instrument. However, according to an alternative embodiment, the system can be configured to generate a graphical depiction of a surgical instrument that actually resembles that specific instrument being monitored by the system. Thus, for example, if the system were being used to track the position and orientation of a rigid endoscope, the central controller could be configured to visually depict the instrument on the display means as a rigid endoscope. In another example, if the system were tracking the position and orientation of a surgical implant, the system could be configured to display a graphical likeness of the implant on the display means used by the surgeon to monitor the actual position and orientation of the implant.

According to one alternative embodiment, an actual surgical instrument being tracked by the system would be represented on the display means by a corresponding graphical object programmed in by a user. Alternatively, a plurality of different size and shape graphical objects, corresponding to different surgical instruments, can be preprogrammed into the central controller. A user then simply selects the preprogrammed graphical object that most closely resembles the surgical instrument that is to be tracked by the system.

According to a still further embodiment, the central controller automatically selects a preprogrammed graphical object that most closely resembles the actual surgical instrument to be tracked based upon an identification code or other data encoded in some form of memory associated with the instrument. Thus, for example, upon connecting a semi-rigid endoscope to the system, the central controller would query a memory of the endoscope, such as by optically scanning a barcode on the endoscope, or reading data from an associated wireless RFID tag or hard-wired memory chip associated with the endoscope. Upon retrieval of certain identification data for that specific endoscope, the central controller would search either a local or remote database and determine the most appropriate graphical object to use to represent that specific endoscope on the display means.

Figure 8:
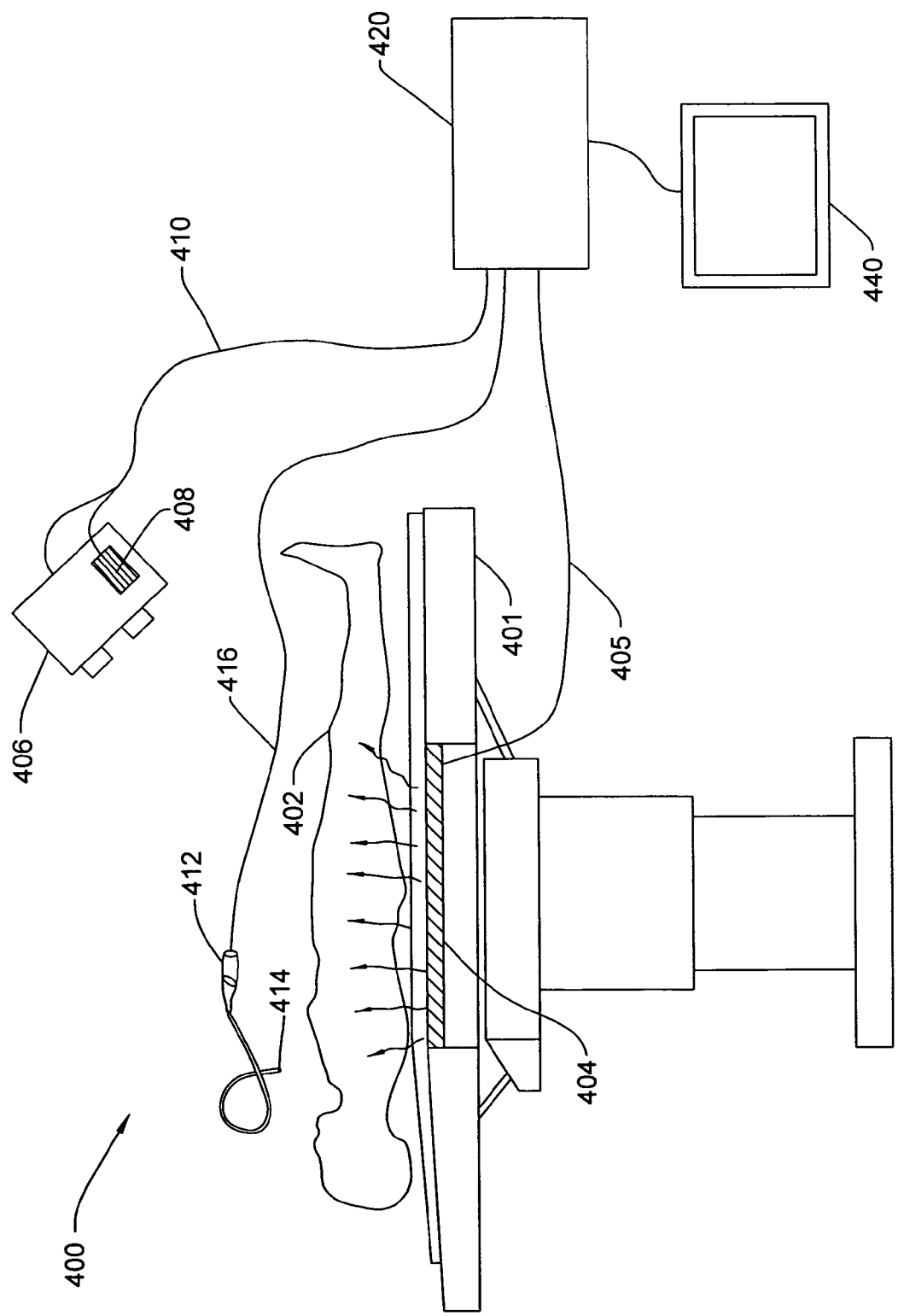
FIG. 8 illustrates a system for tracking the 3-D position and orientation of a surgical instrument according to a further embodiment of the present invention.

FIG. 8 illustrates a further embodiment of the present invention. Similar to FIG. 3, the system 400 illustrated in FIG. 8 includes a stereoscopic camera 406 and associated EMF sensor 408, a central controller 420, display means 440, and one or more surgical instruments 412, such as a flexible endoscope, that includes one or more EMF sensors 414 incorporated therein. However, instead of a smaller, more point-source-like EMF generator as previously disclosed, the present embodiment utilizes a larger, flat EMF generator 404 that can be mounted upon, underneath or within the surgical table 401, and which transmits an electromagnetic wireless signal that more effectively overcomes electromagnetic interference caused by the ferrous metal components sometimes found in surgical tables.

Figure 9:
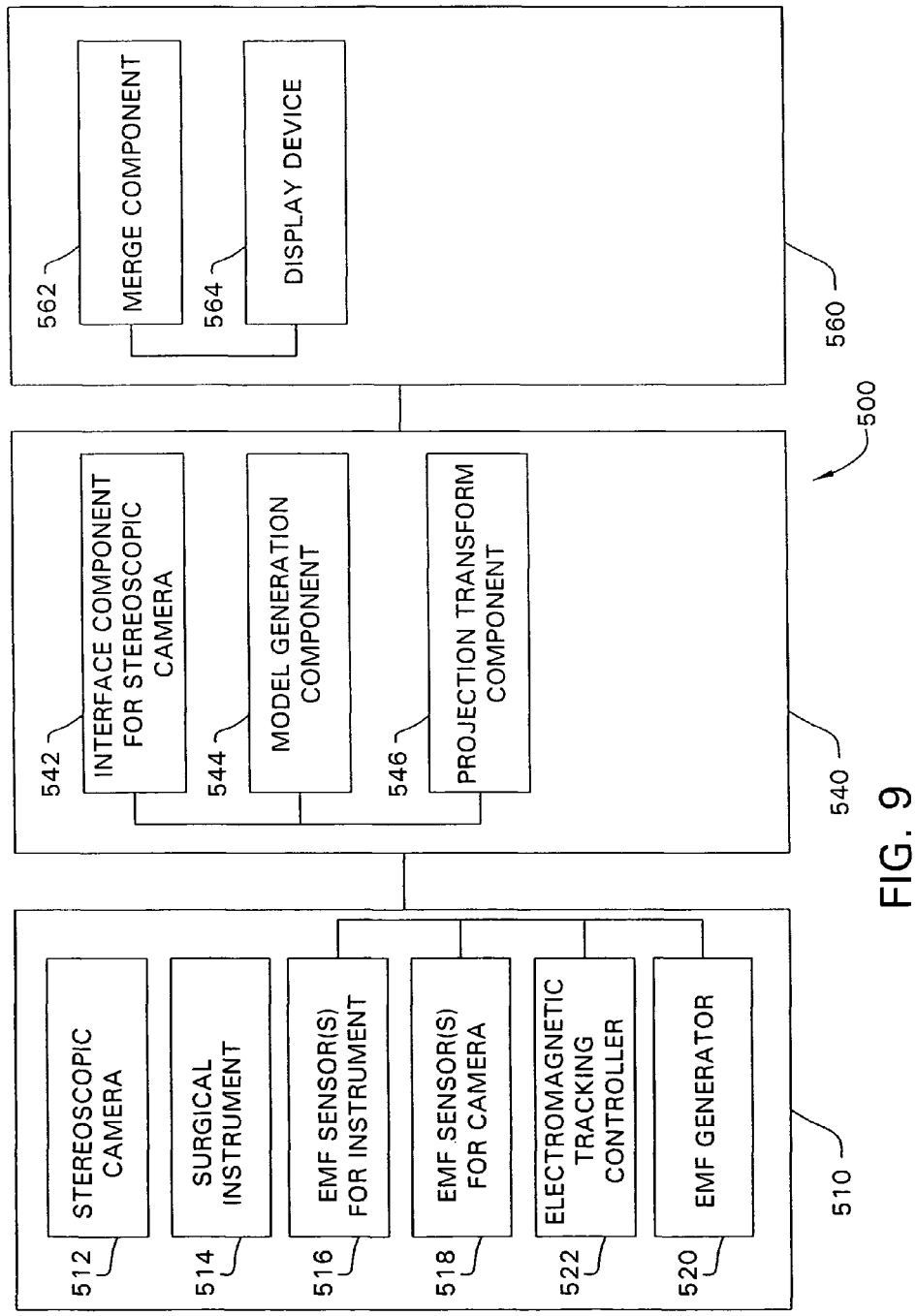
FIG. 9 illustrates a system for tracking the 3-D position and orientation of a surgical instrument according to an additional embodiment of the present invention.

According to an additional embodiment of the present invention, a surgical instrument position and orientation tracking system 500 comprises at least three subsystems. As illustrated in FIG. 9, a tracking subsystem 510 operates to provide real-time position data indicative of the position and orientation of one or more surgical instruments being tracked by the system 500. Included in tracking subsystem 510 are a stereoscopic camera system 512, at least one surgical instrument 514 for remotely viewing and manipulating tissue, at least one EMF sensor 516 incorporated into or attached to the surgical instrument, at least one EMF sensor 518 incorporated into or attached to the stereoscopic camera system, an EMF generator 520 for transmitting a wireless tracking signal, and an electromagnetic tracking controller 522 to coordinate and control the EMF generator and various EMF sensors.

Also included in system 500 is a data processor subsystem 540. Included in subsystem 540 are an interface component 542 for the stereoscopic camera system, which is capable of capturing and providing real-time intra-operative 2-D scans of the patient body. Also included is a model generation component 544 for generating graphical models used to indicate the position and orientation of the surgical instrument being tracked. Lastly included is a projection transform component 546 for computing a perspective projection of a given 3-D point to a point on a given plane.

System 500 also includes a user interface subsystem 560 which operates to provide audio and visual output to the surgeon as well as accept user input. Included in subsystem 560 are a display device 564 capable of rendering video signal data acquired by one or more surgical instruments, such as an endoscope, as well as the stereoscopic camera system. A merge component 562 operates to mix the graphical model representing the surgical instrument with the stereoscopic images of the patient body generated by the stereoscopic camera system 512, thereby producing a video signal capable of being rendered by the display device.

Figure 10:
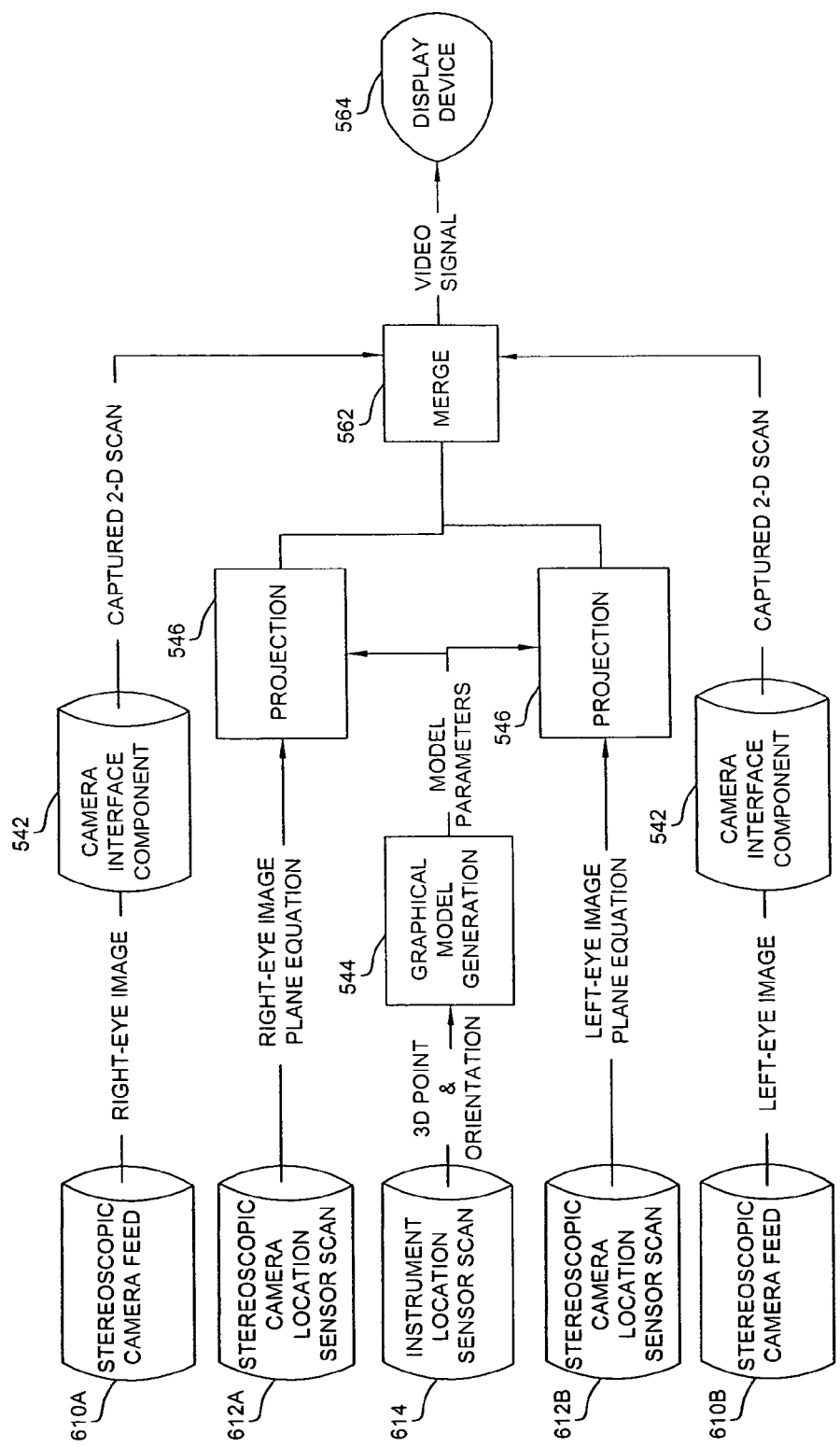
FIG. 10 is a chart depicting the flow and processing of data in the system illustrated in FIG. 9.

The general operation of the surgical instrument position and orientation tracking system 500 is illustrated in the diagram of FIG. 10. Right and left camera feeds 610A and 610B, respectively, are generated by the stereoscopic camera system 512 and provided to the camera interface component 542, which generates 2-D scans of the patient body. These right and left 2-D scans are subsequently provided to the merge component 562 to generate one or more stereoscopic images of the patient body. At the same time, one or more camera location sensor scans 612A and 612B allow the system to determine the location of the cameras relative to the EMF generator 520, and thus be able to represent each 2-D camera scan as an image plane equation having a known relative position. These camera location sensor scans 612A and 612B are fed into the projection transform component 546, which is subsequently able to associate relative position and orientation to the stereoscopic image(s) of the patient body. Simultaneously, instrument location sensor scans 614 provide real-time positional and orientation information for the surgical instrument 514 relative to the EMF generator 520. This instrument location sensor scan data 614 is first provided to the model generation component 544, which generates a model or graphical representation of the surgical instrument that can subsequently be rendered on the display device 564. The instrument location sensor data 614 and associated instrument graphical model data 544 are then provided to the projection transform component 546. Here, the instrument location data is related to the camera location data based on their common frame of reference (that being their position relative to the EMF generator 520). All of this data is then relayed to the merge component 562, which superimposes the graphical model of the surgical instrument being tracked with the dual 2-D camera scans and generates a video signal representing a stereoscopic image of the patient body superimposed with a graphical representation indicative of the relative position and orientation of the surgical instrument. The subsequent video signal generated by the merge component 562 is then relayed to the display device 564 where it can be viewed by the surgeon.

In the embodiments described above, real-time tracking of a surgical instrument's 3-D position and orientation is accomplished by means of a stereoscopic camera system utilized in combination with an electromagnetic field (EMF) generator and associated EMF sensors. During operation of the system, the EMF generator transmits a wireless signal that travels throughout an area of space surrounding the surgical table. An EMF sensor detects the magnetic field, associated with the wireless signal and generates a corresponding signal that gets forwarded to a central controller and processed by one or more predefined algorithms to determine the exact 3-D position and orientation of the EMF sensor relative to the EMF generator that is the source of the magnetic field. Physical displacement of an EMF sensor results in subtle changes in the magnetic field detected by the sensor, which in turn are translated into new 3-D position coordinates (X, Y, Z) and/or orientation coordinates (yaw, pitch, and roll) for the sensor relative to the EMF generator.

The above-described process of magnetic position sensing relies on the use of anisotropic magneto-resistive (AMR) sensors that are capable of detecting the relative intensity and direction of a magnetic field which can subsequently be quantified electronically. Examples of an appropriate EMF generator and AMR sensor that can be utilized in the above embodiments include the multi-axis transmitter and associated 1.3 and 1.8 mm microBIRD™ sensors manufactured by Ascension Technology Corporation and discussed in greater detail in U.S. Pat. No. 6,754,596, the disclosure of which is herein incorporated by reference.

Figure 11:
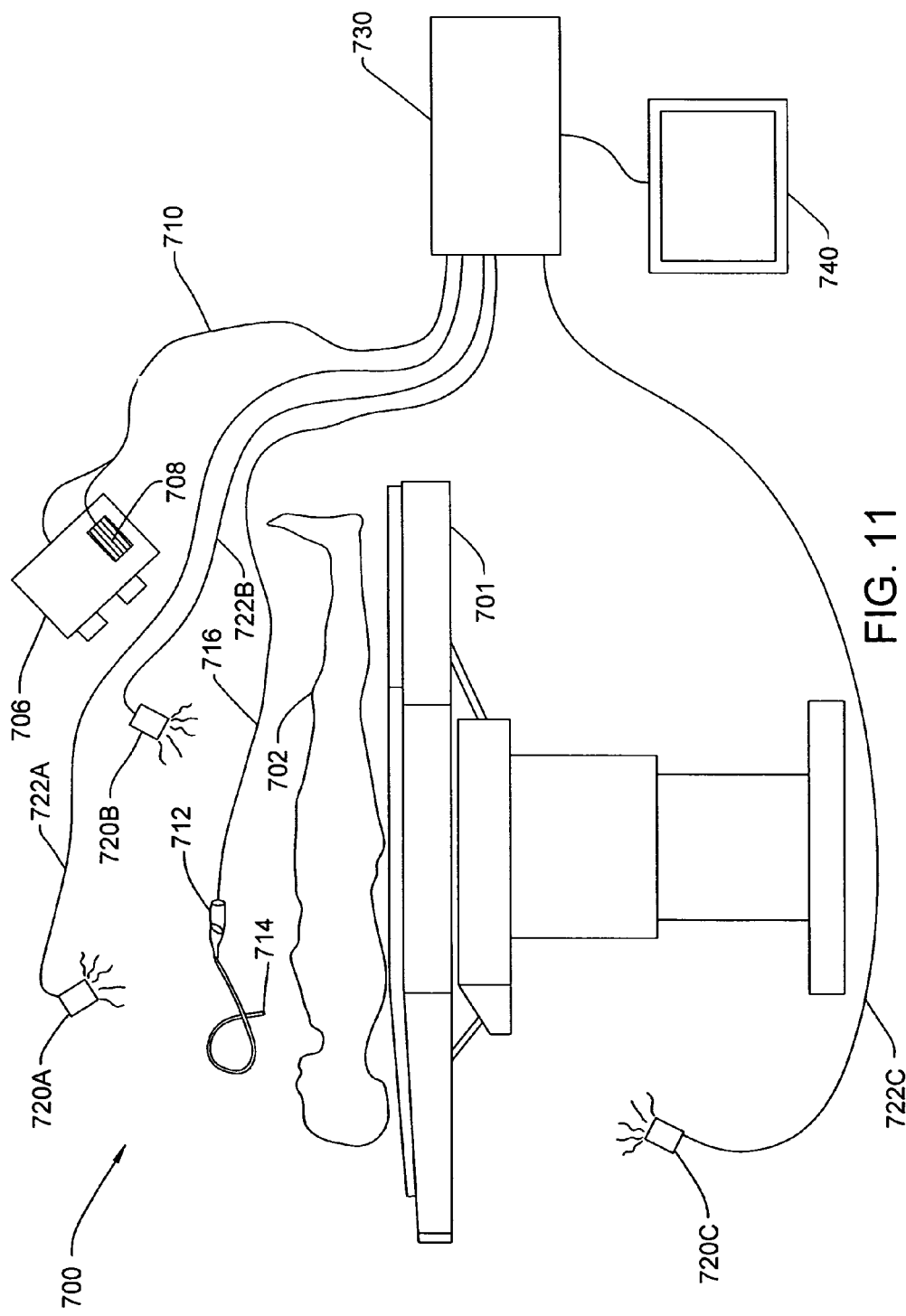
FIG. 11 illustrates a system for tracking the 3-D position and orientation of a surgical instrument utilizing multiple transmitters in accordance with an additional embodiment of the present invention.

Beyond magnetic position sensing technology, the present invention can be configured to operate using other wireless tracking technology. For instance, consider FIG. 11, which illustrates another system for tracking the position of a surgical instrument during a medical procedure. Similar to previous embodiments, the tracking system 700 includes a stereoscopic camera system 706 for acquiring stereoscopic images of the patient body 702. As in prior embodiments, the current system 700 also includes a central controller 730 and a display means 740. However, unlike prior embodiments, system 700 does not utilize a single EMF generator for creating a magnetic field that can be detected by a plurality of EMF sensors associated with the surgical instrument and camera system. Instead, system 700 incorporates a minimum of three wireless transmitters 720A, 720B and 720C distributed at three known, static locations in space around the surgical table. The surgical instrument 712 that is to be tracked incorporates, or has mounted thereupon, a sensor 714 capable of simultaneously receiving each of the wireless signals originating from the three transmitters 720. Then in a manner similar in operation to the U.S. military global positioning satellite (GPS) network, each of the wireless transmitters 720A-720C generate their own time-encoded wireless signal. As the surgical instrument 712 is used, its sensor 714 receives all three wireless signals and forwards them over connection 716 to central controller 730. By then comparing its own synchronized time clock to the time code contained in each of the three wireless signals, central controller 730 can determine for any point in time the distance that exists between the instrument sensor 714 and each of the three wireless transmitters 720A-720C. By then utilizing computational methods such as 3-D trilateration or triangulation, the central controller 730 can determine the specific 3-D position and orientation of instrument sensor 714, and thus the position and orientation of surgical instrument 712 itself. The same process is repeated for the endoscopic camera system 706 utilizing camera sensor 708. Consequently, the 3-D position of both the camera sensor 708 and instrument sensor 714 are determined relative to the same frame of reference (that being the three wireless transmitters 720). From this point on, system 700 operates in the same manner as the previously described embodiments, with the system 700 rendering upon display means 740 one or more stereoscopic images of the patient body 702 that are superimposed with some form of graphical representation of surgical instrument 712 that indicates the position and orientation of the instrument relative to the patient body.

In yet another embodiment of the invention, an instrument tracking system does not generate a stereoscopic image of the patient body on a display, nor superimpose some form of graphical object corresponding to the surgical tool upon the display. Instead, when a controller of the system determines the actual position of a surgical instrument within the patient body, the controller initiates the projection of some form of light beam (i.e., low power laser) directly upon the patient body. As the instrument proceeds to move, the light beam projected upon the patient body will proceed to track the movement of the instrument. Thus, instead of superimposing a graphical representation of a surgical instrument upon a stereoscopic image of the patient body and rendering the combined image upon a display, the immediate embodiment projects an instrument image or other graphical representation of the surgical instrument upon the actual patient body.

According to variation of the above embodiment, a tracking system would include, among other things, an EMF generator, one or more EMF sensors associated with a surgical instrument, means for projecting a light beam upon the patient body, and one or more EMF sensors associated with the projector so that the system could determine the three-dimensional location of the projector relative to the EMF generator.

In an additional embodiment of the present invention, one or more of the systems as described above are modified to include two or more stereoscopic camera systems positioned at different locations around the patient body. As a result, the modified system is able to generate multiple stereoscopic views, with each view representing the patient body from a different perspective.

In the previously discussed embodiments, the stereoscopic camera or cameras were positioned around the patient body at presumably fixed locations. However, according to an alternative embodiment, one or more of the stereoscopic cameras in the system are not in a fixed position, but instead are mobile. In a first example, the camera is movably mounted such that it can be repositioned during the surgical procedure in order to obtain a stereoscopic view of the patient body from a different perspective. According to a second example, the camera is portable and can be carried by or mounted upon a member of the surgical staff. For instance, the camera could be configured to be worn by the surgeon as eyewear or headwear, resulting in the camera tracking the movement of the surgeon. Consequently, the camera will capture and generate a stereoscopic image of the area of the patient body currently being looked at by the surgeon. The advantage of such a system is that it allows the surgeon to obtain stereoscopic images of the patient body from numerous perspectives.

In a similar embodiment, the system includes a stereoscopic camera that is mounted upon or worn by the surgeon, such as, for example, as eyewear or headwear. However, according to the immediate embodiment, the camera includes zooming capabilities that can automatically adjust based on the distance between the camera and the patient body. For example, the camera could be configured to automatically zoom in and out by a predetermined or calculated amount in response to the surgeon getting closer or farther away from the patient body. According to another example, the system can be configured to automatically adjust the scale of the displayed stereoscopic image, including the depiction of the patient body and graphical object representing the surgical instrument, in response to the zoom level of the camera.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A method for tracking the three-dimensional position of a flexible surgical instrument while the instrument is being utilized within a patient body during a surgery, comprising the steps of:
   providing a flexible surgical instrument;
   capturing a stereoscopic image of an exterior of the patient body during the surgery;
   wirelessly determining the three-dimensional position of the patient body relative to a first reference point;
   wirelessly determining the three-dimensional position of the flexible surgical instrument disposed within the patient body relative to the first reference point;
   calculating the three-dimensional position of the flexible surgical instrument disposed within the patient body relative to the patient body;
   obtaining a graphical representation of the flexible surgical instrument disposed within the patient body;
   superimposing the graphical representation of the flexible surgical instrument disposed within the patient body and its three-dimensional position upon the captured stereoscopic image of the exterior of the patient body; and
   displaying the stereoscopic image of the exterior of the patient body and the graphical representation of the flexible surgical instrument on a display device,
   wherein the step of displaying the stereoscopic image of the exterior of the patient body on the display device comprises displaying two 2-D graphical representations of the exterior of the patient body taken from significantly different perspectives, and the step of superimposing a graphical representation of the flexible surgical instrument upon the stereoscopic image comprises graphically displaying the graphical representation of the flexible surgical instrument on each of the two graphical representations of the exterior of the patient body so that a user can determine the location of the flexible surgical instrument within the patient body.

2. The method according to claim 1, including the steps of:
   wirelessly determining the three-dimensional orientation of the patient body and a distal tip of the flexible surgical instrument disposed within the patient body relative to the first reference point; and
   calculating the three-dimensional orientation of the distal tip of the flexible surgical instrument disposed within the patient body relative to the patient body,
   wherein the displayed stereoscopic image of the two graphical representations of the exterior of the patient body and the superimposed graphical representation of the flexible surgical instrument disposed within the patient body displayed on each of the two graphical representations on the display device indicates the three-dimensional position and orientation of the distal tip of the flexible surgical instrument relative to the patient body.

3. The method according to claim 1, comprising the further steps of:
   establishing an external electromagnetic field utilizing an electromagnetic field generator;
   associating at least one electromagnetic field sensor with the stereoscopic camera system;
   disposing at least one electromagnetic field sensor at a distal tip of the flexible surgical instrument;
   detecting the electromagnetic field orientation and intensity at the stereoscopic camera system using the associated electromagnetic field sensor; and
   detecting the electromagnetic field orientation and intensity at the distal tip of the flexible surgical instrument disposed within the patient body using the associated electromagnetic field sensor.

4. The method according to claim 3, wherein the location of the electromagnetic field generator represents the first reference point.

5. The method according to claim 1, wherein the graphical representation of the flexible surgical instrument is manually selected by a user.

6. The method according to claim 1, wherein the graphical representation of the flexible surgical instrument is automatically selected based upon identification data retrieved from the flexible surgical instrument.

7. The method according to claim 3, wherein the superimposed graphical representation of the flexible surgical instrument displayed on each of the two graphical representations of the exterior of the patient body indicates a current position of the at least one electromagnetic field sensor that is disposed at the distal tip of the flexible surgical instrument.

8. The method according to claim 3, wherein the superimposed graphical representation of the flexible surgical instrument displayed on each of the two graphical representations of the exterior of the patient body simultaneously indicates a former position as well as a current position of the at least one electromagnetic field sensor disposed at the distal tip of the flexible surgical instrument.

9. The method according to claim 1, comprising the further steps of:
   transmitting a time-encoded wireless signal from each of at least three wireless transmitters having a known three-dimensional position;

associating at least one wireless signal receiver with the stereoscopic camera system;

disposing at least one wireless signal receiver at a distal tip of the flexible surgical instrument;

detecting the three time-encoded wireless signals at the stereoscopic camera system using the associated wireless signal receiver; and detecting the three time-encoded wireless signals at the distal tip of the flexible surgical instrument using the associated wireless signal receiver.

10. The method according to claim 9, wherein the three wireless transmitters represent the first reference point.

11. The method according to claim 1, including the steps of:

wirelessly determining the orientation of the patient body;

wirelessly determining the orientation of a distal tip of the flexible surgical instrument disposed within the patient body; and the step of superimposing the graphical representation of the flexible surgical instrument upon each said graphical representation of the exterior of the patient body includes displaying the two graphical representations of the exterior of the patient body in a determined orientation and a superimposed graphical representation of the distal tip of the flexible surgical instrument disposed within the patient body in a determined orientation on the two graphical representations.

12. A method of tracking the position of a flexible surgical instrument as the instrument is being utilized within a patient body during a surgery, comprising the steps of:

capturing a stereoscopic image of an exterior of the patient body during the surgery from at least one perspective with a stereoscopic camera;

wirelessly determining the position of a distal tip of the flexible surgical instrument located within the patient body;

obtaining a graphical representation of the distal tip of the flexible surgical instrument disposed within the patient body;

superimposing the graphical representation of the flexible surgical instrument located within the patient body upon the stereoscopic image of the exterior of the patient body indicating the three-dimensional position of the distal tip of the surgical instrument located within the patient body relative to the patient body; and displaying the stereoscopic image of the exterior of the patient body and the superimposed graphical representation of the flexible surgical instrument on a display device.

13. The method according to claim 12, including the steps of:

wirelessly determining the three-dimensional position and orientation of the patient body relative to a first reference point;

wirelessly determining the three-dimensional position and orientation of the distal tip of the flexible surgical instrument located within the patient body relative to the first reference point;

wirelessly determining the position of the stereoscopic camera relative to the first reference point; and the step of superimposing the graphical representation of the flexible surgical instrument located within the patient body upon the stereoscopic image of the exterior of the patient body comprising calculating the three-dimensional position and the orientation of the distal tip of the flexible surgical instrument disposed within the patient body relative to the patient body and to the stereoscopic camera.

14. The method according to claim 13, wherein the three-dimensional position and the orientation of the distal tip of the flexible surgical instrument are determined in near real-time.

15. The method according to claim 13, wherein the flexible surgical instrument comprises a flexible endoscope, the method further comprising the steps of:

mounting a plurality of sensors along at least a portion of the length of an insertion tube of the flexible endoscope; and inserting the insertion tube including the plurality of sensors into the patient body for wireless sensing thereof.

16. The method according to claim 1, wherein the flexible surgical instrument comprises a flexible endoscope, the method further comprising the steps of:

mounting a plurality of sensors along at least a portion of the length of an insertion tube of the flexible endoscope; and inserting the insertion tube including the plurality of sensors into the patient body for wireless sensing thereof.

17. The method according to claim 13, including the steps of:

mounting the stereoscopic camera onto a body of a person involved in performing a surgery; and providing one of eyewear and headwear as the display device and mounting the one of eyewear and headwear onto the body of the person involved in performing a surgery.

18. The method according to claim 12, further comprising the step of capturing first and second stereoscopic images of the exterior of the patient body and displaying the images on the display device, the first stereoscopic image being from a first perspective, and the second stereoscopic image being from a second perspective that is different from the first perspective to provide a three-dimensional image of the exterior of the patient body.

19. The method according to claim 12, wherein the step of displaying the stereoscopic image of the exterior of the patient body on a display device comprises two 2-D graphical representations of the patient body taken from significantly different perspectives, and the step of superimposing a graphical representation of the flexible surgical instrument upon the stereoscopic image is graphically displayed on each of the graphical representations of the patient body so that a user can determine the location of the flexible surgical instrument within the patient body.

20. The method according to claim 12, wherein the flexible surgical instrument comprises a flexible endoscope having one or more controls on the body thereof, the method including the step of:

manipulating or bending the distal tip of the flexible endoscope during insertion of the flexible endoscope into the interior of the patient body.

21. The method according to claim 1, wherein the flexible surgical instrument comprises a flexible endoscope having one or more controls on the body thereof, the method including the step of:

manipulating or bending the distal tip of the flexible endoscope during insertion of the flexible endoscope into the interior of the patient body.

22. A method of tracking the position of a surgical instrument as the instrument is being utilized within a patient body during a surgery, comprising the steps of:

capturing a stereoscopic image of an exterior of the patient body from at least one perspective with a stereoscopic camera;

displaying the stereoscopic image of the exterior of the patient body on a display device;

manipulating or bending a distal tip of the flexible surgical instrument during insertion and advancement through the interior of the patient body;

wirelessly determining the position of the distal tip of the flexible surgical instrument located within the patient body; and superimposing a graphical representation of the distal tip of the flexible surgical instrument upon the captured stereoscopic image of the exterior of the patient body indicating the three-dimensional position of the flexible surgical instrument relative to the patient body.

23. The method according to claim 22, including the steps of:

wirelessly determining the three-dimensional position and orientation of the patient body relative to a first reference point;

wirelessly determining the three-dimensional position and orientation of the distal tip of the flexible surgical instrument relative to the first reference point;

wirelessly determining the position of the stereoscopic camera relative to the first reference point; and the step of superimposing the graphical representation of the distal tip of the surgical instrument upon the captured stereoscopic image of the exterior of the patient body comprising calculating the three-dimensional position and the orientation of the distal tip of the flexible surgical instrument relative to the patient body and to the stereoscopic camera.

24. The method according to claim 23, wherein the step of wirelessly determining the three-dimensional position and orientation of the distal tip of the flexible surgical instrument relative to the first reference point comprises:

providing an electromagnetic field generator at the first reference point;

disposing an electromagnetic field sensor at the distal tip of the flexible surgical instrument, and detecting the electromagnetic field orientation and intensity with the electromagnetic field sensor at the distal tip of the flexible surgical instrument that is disposed within the patient body relative to the electromagnetic field generator at the first reference point.

25. The method according to claim 22, including the steps of:

mounting the stereoscopic camera onto a body of a person involved in performing a surgery; and providing one of eyewear and headwear as the display device and mounting the one of eyewear and headwear onto the body of the person involved in performing a surgery.

26. The method according to claim 22, further comprising the step of capturing first and second stereoscopic images of the exterior of the patient body and displaying the images on the display device, the first stereoscopic image being from a first perspective, and the second stereoscopic image being from a second perspective that is different from the first perspective to provide a three-dimensional image of the exterior of the patient body.

27. The method according to claim 23, wherein the flexible surgical instrument comprises a flexible endoscope, the method further comprising the step of mounting a plurality of electromagnetic sensors along at least a portion of the length of an insertion tube of the endoscope for wireless sensing and display thereof.

28. The method according to claim 22, comprising the further steps of:

transmitting a time-encoded wireless signal from each of at least three wireless transmitters having a known three-dimensional position;

associating at least one wireless signal receiver with the stereoscopic camera system;

disposing at least one wireless signal receiver at the distal tip of the flexible surgical instrument;

detecting the three time-encoded wireless signals at the stereoscopic camera system using the associated wireless signal receiver; and detecting the three time-encoded wireless signals at the distal tip of the flexible surgical instrument using the wireless signal receiver disposed thereat.

29. The method according to claim 22, including providing polarizing or filtering glasses for viewing the stereoscopic image and the superimposed graphical representation on a display device.

* * * * *